United States Patent [19]

Farmer, Jr. et al.

[11] 4,396,766

[45] Aug. 2, 1983

[54] PROCESS FOR PRODUCING SODIUM AND ZINC PYRITHIONE

[75] Inventors: Douglas A. Farmer, Jr., Madison; Lawrence E. Katz, Orange, both of Conn.

[73] Assignee: Olin Corporation, New Haven, Conn.

[21] Appl. No.: 372,510

[22] Filed: Apr. 28, 1982

[51] Int. Cl.$^3$ .......................................... C07D 213/89
[52] U.S. Cl. ...................................... 546/6; 546/290
[58] Field of Search .................................. 544/6, 290

[56] References Cited

U.S. PATENT DOCUMENTS

| | | | |
|---|---|---|---|
| 2,686,786 | 8/1954 | Bernstein | 546/290 |
| 3,159,640 | 12/1964 | Shermer | 546/290 |
| 3,759,932 | 9/1973 | Gavin et al. | 546/290 |

FOREIGN PATENT DOCUMENTS 56-1051254  6/1981  Japan.

*Primary Examiner*—Mark L. Berch
*Attorney, Agent, or Firm*—W. A. Simons; T. P. O'Day

[57] ABSTRACT

Disclosed is a process for producing a zinc pyrithione product having an acceptable white or off-white color and containing substantially no undesired 2-hydroxypyridine-N-oxide or metal salt complexes thereof, by
  (1) making sodium pyrithione by reacting a 2-halopyridine-N-oxide with sodium hydrosulfide and sodium carbonate (or a mixture of sodium carbonate and sodium hydroxide) under selected addition temperatures and reaction temperatures and in selected mole ratios; followed by
  (2) making zinc pyrithione by reacting the sodium pyrithione with a zinc salt.

12 Claims, No Drawings

PROCESS FOR PRODUCING SODIUM AND ZINC PYRITHIONE

BACKGROUND OF THE INVENTION

1. Field of the Invention

The present invention relates to a process for making a zinc pyrithione product having an acceptable white or off-white color and containing substantially no undesired 2-hydroxypyridine-N-oxide or metal salt complexes thereof.

2. Description of the Prior Art

Zinc pyrithione [also known as zinc pyridine-2-thiol-N-oxide or bis[1-hydroxy-2(H) pyridinethionato]-zinc] is an excellent biocide. It has been employed as a broad-spectrum anti-microbial agent and preservative in metalworking fluids, plastics, and cosmetics. Its principal use is as an antidandruff agent in hair products. Sodium pyrithione [also called the sodium salt of 1-hydroxy-2-pyridinethione, sodium pyridine-2-thiol-N-oxide, or 2-pyridinethiol-1-oxide, Na salt] is also employed as a preservative in various applications (e.g., metalworking fluids).

The generally accepted route for making these compounds is by the mercaptization of a 2-halopyridine-N-oxide with an alkali metal sulfide or hydrosulfide and a base to make an alkali metal pyrithione and then converting this alkali metal salt to zinc pyrithione by reaction with a zinc salt (e.g., $ZnCl_2$ or $ZnSO_4$).

One preferred method for making sodium pyrithione by this route is disclosed in Japanese Pat. No. 1,051,254 which was filed by Pivawer, Schiessl, and Shermer on Apr. 19, 1977, and issued on June 25, 1981. Their method prepared sodium pyrithione by reacting 2-chloropyridine-N-oxide with a substantially equimolar amount or a slight molar excess of NaSH (i.e., from 1 to 1.25 moles per mole of N-oxide). A critical parameter of their process was controlling the pH of the reaction in the range from 7.5 to 11.0. They taught control of the pH could be carried out by adding NaOH simultaneously or concurrently with the NaSH at regulated feed rates.

It should be noted that this method disclosed by Pivawer et al. in their specific examples employed an NaSH and NaOH addition temperature of not less than 75° C. Furthermore, this Japanese patent teaches that alkali metal carbonates may be substituted for NaOH as pH control agents; however, none of the specific examples employed an alkali metal carbonate. In all, no known publication has ever taught the advantages associated with the use of sodium carbonate (e.g., higher yields and a whiter product) as a base when making sodium or zinc pyrithione.

Several problems arise when using this process of Pivawer et al. on large-scale commercial production runs. First, because NaOH and NaSH are highly corrosive, it is difficult to obtain accurate pH readings or keep pH meters operating reliably. Also, the amount of the by-product 2-hydroxypyridine-N-oxide produced will increase when NaOH is used solely as a base in the formation of sodium pyrithione. Formation of this by-product decreases the yields of both sodium and zinc pyrithione and causes impure products to be made.

Besides these difficulties, it should be noted that sodium pyrithione and zinc pyrithione occasionally have problems meeting strict color specifications set by formulators of cosmetics and toiletries. Since the esthetics of cosmetics and toiletries normally require certain desirable colors and the formulators of such products go to great lengths to achieve specific color effects, any ingredient which varies very much from white or colorless may make the colorant formulators' task very difficult. In the cases of sodium and zinc pyrithione, it is believed that unacceptable discoloration results from the presence of unwanted traces of contaminants during the making of the sodium pyrithione. One method of removing these contaminants is to carry out multi-step purification processes. This is costly and adds extra processing steps.

Accordingly, there is a need in the art to overcome the above-stated problems associated with the Pivawer et al. process. Also, there is a need for a better method of preventing or removing unacceptable discoloration of sodium or zinc pyrithione. It is believed that the present invention which involves the making of sodium pyrithione by reacting a 2-halopyridine-N-oxide with $Na_2CO_3$ (or a mixture of NaOH and $Na_2CO_3$) and NaSH under selected addition temperatures and reaction temperatures and in selected mol ratios meets these needs.

BRIEF DESCRIPTION OF THE INVENTION

The present invention, therefore, is directed to a process for making zinc pyrithione, which comprises the steps:

(a) adding sodium hydrosulfide and a base selected from the group consisting of sodium carbonate and sodium hydroxide to an aqueous solution of a 2-halopyridine-N-oxide selected from the group consisting of 2-bromopyridine-N-oxide and 2-chloropyridine-n-oxide at a temperature below about 70° C.
  (i) wherein the mole ratio of the sum of moles of said sodium hydrosulfide and said base to said 2-halopyridine-N-oxide is at least about 2:1;
  (ii) wherein the mole ratio of said sodium hydrosulfide to said 2-halopyridine-N-oxide is at least about 1:1;
  (iii) wherein the mole ratio of said base to said 2-halopyridine-N-oxide is at least about 0.75:1.0; and
  (iv) wherein said base is comprised of at least about 10 mole % of sodium carbonate;
(b) heating the resultant mixture of step (a) to about 75° C. to about 105° C. for sufficient time to form sodium pyrithione; and
(c) reacting said sodium pyrithione with a zinc salt to form zinc pyrithione.

DETAILED DESCRIPTION

The present invention encompasses a three-step reaction sequence wherein a 2-halopyridine-N-oxide is first reacted with sodium hydrosulfide to form 2-mercaptopyridine-N-oxide. This latter compound is then converted to sodium pyrithione by reaction with a sodium-containing base (e.g. $NaCO_3$ or NaOH, or both). The sodium pyrithione is then converted to zinc pyrithione by reaction with a zinc salt (e.g. $ZnCl_2$ or $ZnSO_4$). These reactions are illustrated by the following reactions (A), (B) and (C) wherein 2-chloropyridine-N-oxide is employed as the 2-halopyridine-N-oxide, $Na_2CO_3$ is the sole base and $ZnCl_2$ is employed as the zinc salt:

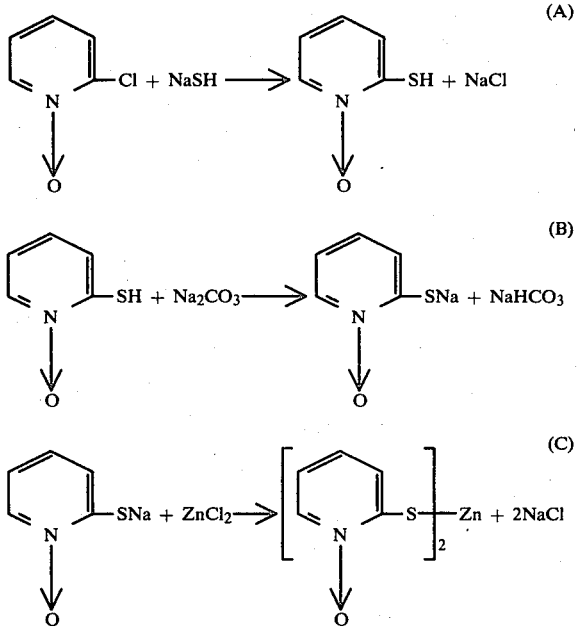

As stated above, the 2-halopyridine-N-oxide reactants of the present process may be either 2-bromopyridine-N-oxide or 2-chloropyridine-N-oxide. Both of these compounds are well known and may be made by a variety of ways, including the oxidation of the corresponding 2-halopyridine with an oxidizing agent such as peracetic acid. Of the two compounds, 2-chloropyridine-N-oxide is preferred because of cost considerations.

The sodium hydrosulfide (also called sodium sulfhydrate) reactant is also a well-known chemical and is made by many conventional methods. It may be generated in situ by addition of $H_2S$ to a mixture of base and 2-chloropyridine-N-oxide.

The presence of a certain amount of sodium carbonate (i.e., at least about 10 mole % of the base) is also a critical feature of the present invention. The use of too much NaOH as the base will increase the amount of the by-product 2-hydroxypyridine-N-oxide produced. The formation of this by-product will decrease yield of sodium pyrithione, and, in turn, the yield of zinc pyrithione. But, in some instances, NaOH is useful as a co-base. Accordingly, one preferred embodiment of the present invention is to use an optimum combination of $Na_2CO_3$ and NaOH as co-bases. The most preferred embodiment is the use of $Na_2CO_3$ alone.

In accordance with the present invention, the sodium hydrosulfide and base are first added to an aqueous solution of the 2-halopyridine-N-oxide at a temperature below about 70° C. Generally, an aqueous solution is employed as the reaction medium because the water acts as an effective solvent and heat transfer medium. Furthermore, 2-halopyridine-N-oxides such as 2-chloropyridine-N-oxide are normally prepared in aqueous solutions and it facilitates processing to not remove this reactant from the water. The amount of water present in this process is not critical, but from about 2- to about 15-fold excess by weight of $H_2O$ over the 2-halopyridine-N-oxide is preferred. Too much water is not desirable because it raises processing costs. The sodium hydrosulfide and base are preferably added neat (or without water) to minimize processing costs by maximizing batch productivity.

The addition step (a) may be conducted at any temperature under about 70° C., suitably from ambient (about 20° C.) to about 65° C. If the reactants are combined together at too high a reaction temperature, an uncontrollable exotherm may occur. Furthermore, it is believed that yields of sodium and zinc pyrithione will suffer if the addition temperature is too high.

The addition time should be as rapid as possible so that the above-stated molar ratios of reactants are present in the resultant mixture prior to heating above about 70° C. It is preferred to add both the sodium hydrosulfide and the base quickly and simultaneously to the 2-halopyridine-N-oxide in order to save processing time. But, it may be suitable to add either reactant before the other in a sequential order. However, it should be noted that the exact mode and rate of addition are not critical parameters. In contrast, the process described by Pivawer et al. required critical rates of additions in order to control the reaction pH. Thus, the present invention does not require expensive chemical metering and pH measuring equipment which the prior art process needed.

At least a subsantially equimolar amount of the sodium hydrosulfide per mole of 2-halopyridine-N-oxide substrate is employed in the present reaction. If less than equimolar amounts are utilized, there will be insufficient sulfur available to fully convert the 2-halopyridine-N-oxide to 2-mercaptopyridine-N-oxide according to equation (A) above. Preferably, a slight molar excess is utilized, suitably from 1.00 to about 1.25 moles of sodium hydrosulfide per mole of 2-halopyridine-N-oxide, more preferably from about 1.00:1.00 to about 1.15:1.00, and most preferably from about 1.00:1.00 to about 1.10:1.00. Larger amounts of sodium hydrosulfide than the 1.25:1.00 molar ratio may be utilized, but no advantage is seen.

The amount of base added should be sufficient to convert substantially all of any 2-mercaptopyridine-N-oxide formed to sodium pyrithione according to equation (B), above, and depends in part on the amount of excess sodium hydrosulfide added since sodium hydrosulfide may also act as a base and convert 2-mercaptopyridine-N-oxide to sodium pyrithione. Generally, an amount of base should be added such that the ratio of the sum of the moles of base added and the moles of NaSH added to moles of 2-halopyridine-N-oxide present is at least about 2.1, preferably from about 2:1 to about 3:1; more preferably from about 2.00:1 to about 2.45:1; and most preferably from about 2.05:1 to about 2.20:1.

It is believed that the mole ratio of base to 2-halopyridine-N-oxide should be at least 0.75:1 to obtain the desired purity and yields of sodium pyrithione. Preferably, this mole ratio should be from about 1.0:1.0 to about 1.2:1.0.

Once the addition is completed, the reaction to form sodium pyrithione may be conducted over a temperature range from about 75° C. to about 105° C., preferably, from about 80° C. to about 95° C. Reaction temperatures below about 75° C. result in reaction rates too low to be commercially desirable. Reaction temperatures above about 105° C. may cause undesirable side reactions and are inconvenient because they exceed the boiling point of the reaction medium. Reaction time will, of course, vary with the temperature being employed. The time of the reaction is not critical; however, for maximum yield and for obtaining a desirable white color, the reaction time should be minimized. Times from about 30 minutes to about 120 minutes are generally sufficient for completion of the reaction. The reaction is preferably run at atmospheric pressure. Sub- and super-atmospheric pressures may be employed, but require costly additional processing equipment.

After the sodium pyrithione is formed, a zinc salt is then added to the mixture, whereby zinc pyrithione precipitates from the solution.

The amount of zinc salt added should preferably be stoichiometrically sufficient so that the sodium pyrithione is completely reacted. However, a minimum of excess zinc salt should be used for attainment of a desired color. The preferable mole ratios of zinc salt to sodium pyrithione may range from about 0.9:2 to about 1.25:2 more preferably from about 1:2 to about 1.1:2. Any suitable zinc salt which is soluble in an aqueous solution of sodium pyrithione may be used. The preferred salts are $ZnCl_2$, $ZnSO_4$, and hydrates thereof. $ZnSO_4$ is most preferred.

The preferred reaction temperature for making zinc pyrithione is from about 20° C. to about 100° C.; more preferably from about 25° C. to about 95° C. The processing time will vary with the reaction temperature (e.g., from about 10 minutes to about 120 minutes).

When the reaction is complete, the formed zinc pyrithione will precipitate from the solution. This precipitate may be filtered from the reaction mixture and further processed according to conventional means.

The term "discoloration" as employed herein with zinc pyrithione may mean any unacceptable gray, green, red, yellow, blue, brown, or color other than a white or off-white color. The latter are generally suitable in most hair products, cosmetic, and toiletry applications. One way of quantitatively measuring for discoloration in zinc pyrithione is by measuring the Hunter color parameters and calculating a whiteness value from them (note Examples below). It should be noted that the causes of discoloration in sodium pyrithione solutions and zinc pyrithione made from the former are not clearly known. It is believed one possible cause is oxidation of contaminants during further processing of sodium pyrithione.

The present invention also encompasses the formation of other alkali metal pyrithiones besides sodium. If potassium pyrithione was made, then potassium carbonate (or a mixture of potassium carbonate and potassium hydroxide) would be employed with potassium hydrosulfide.

The following Examples and Comparisons are illustrative of preferred embodiments of the present invention. All parts and percentages are by weight unless explicitly stated otherwise.

Examples I, II, and III, compared to their corresponding Comparisons I, II, and III, illustrate that using sodium carbonate works on three different samples of 2-chloropyridine-N-oxide; each sample yields zinc pyrithione with different color parameters, however, the use of carbonate improves all of them. Yields are also raised by the use of carbonate.

Examples IV to VIII, compared to Comparison IV, show the diminution of the 2-hydroxy-pyridine-N-oxide impurity in zinc pyrithione with amount of sodium carbonate substituted for sodium hydroxide. Color also improves with the replacement of hydroxide by carbonate.

EXAMPLE I

To an aqueous solution of 2-chloropyridine-N-oxide (165.3 grams of solution; 0.25 mole of active compound) at 60° C. was added 22.7 grams (0.32 mole) sodium carbonate, 22.7 grams (0.30 mole) sodium hydrosulfide (73.6% by weight active compound), and 45.2 grams water. The solution was stirred at 90° C. for 0.5 hour and then cooled to 60° C. Concentrated hydrochloric acid (46.5 grams) was added, while purging with nitrogen, over a one hour time period. After cooling to 30° C., the mixture was filtered to remove small amounts of sulfur by-products, and an aqueous solution of 20% by weight zinc sulfate (95.9 grams of solution; 0.12 mole of active compound) was added with stirring to the filtrate containing sodium pyrithione. The resulting zinc pyrithione product was filtered to give 117.5 grams (wet cake). Color parameters were determined using a Hunter Color/Difference meter[1]. A portion was dried and analyzed for zinc pyrithione content. A yield of 94.6% (assaying 95.3% pure) was obtained. The Hunter color parameters were found to be: L=92.6; a=−1.4; b=5.6; and calculated Whiteness[2] was W=56.2 (compared to MgO=100).

[1]Measured on a Hunterlab Color/Difference Meter D25D2 manufactured by Hunter Associated Laboratory Inc. of Fairfax, VA, according to AATCC test method 110-1972
[2]Whiteness=$0.01L^2-0.057bL$ The comparison of the results of Example I and Comparison I shows that the Carbonate Procedure of the present invention gives a better yield and a whiter product (especially a lower b value and a higher calculated W value).

COMPARISON I

To the same aqueous solution of 2-chloro-pyridine-N-oxide used in Example I (182.9 grams of solution; 0.28 moles of active compound) at 60° C. in a reaction vessel was added an aqueous solution containing 11.4 grams (0.29 mole) sodium hydroxide, 26.3 grams (0.35 mole) sodium hydrosulfide (73.6% by weight active compound), and 84.4 grams water. The solution was stirred and heated at 93° C. for 0.5 hour and then cooled to 60° C. Concentrated hydrochloric acid (11.4 grams) was added, while purging with nitrogen, over a one hour time period. After cooling to 30° C., the mixture was filtered and an aqueous solution of 20% by weight zinc sulfate (103.0 grams of solution; 0.13 mole of active compound) was added with stirring. The product was filtered to give 124.8 grams (wet cake). Color parameters were determined using a Hunter Color/Difference meter. A portion was dried and analyzed for zinc pyrithione content. A yield of 90.8% product (assaying 95.1% pure) was obtained. The measured color parameters and calculated Whiteness were L=92.8; a=−2.4; b=6.9; W=49.1.

EXAMPLE II

To an aqueous solution of a different sample of 2-chloropyridine-N-oxide (197.7 grams; 0.30 mole) than employed in Example I and Comparison I and 37.8 grams (0.36 mole) sodium carbonate at 50° C. was added a solution of 25.3 grams (0.33 mole) sodium hydrosulfide (73.1% by weight active compound) in 50.0 grams of water. The solution was stirred at 90° C. for one-half hour and then cooled to 60° C. Concentrated hydrochloric acid (52.0 grams) was added, while purging with nitrogen, over a one hour time period. After cooling to 30° C., the mixture was filtered and an aqueous solution of 20% by weight zinc sulfate (109.2 grams of solution; 0.14 mole of active compound) was added with stirring. The product was filtered to give 162.2 grams (wet cake). Color parameters were determined using a Hunter Color/Difference meter. A portion was dried and analyzed for zinc pyrithione content. A yield of 88.4% (assaying 97.0% pure) was obtained. The measured color parameters and calculated Whiteness were: L=92.7; a=−1.2; b=5.9; W=54.4.

The comparison of the results of Example II and Comparison II shows that the Carbonate Procedure gives a better yield and a whiter product.

COMPARISON II

To the same aqueous solution of 2-chloropyridine-N-oxide (197.7 grams of a solution; 0.30 mole) as used in Example II at 50° C. in a reaction vessel was added an aqueous solution containing 11.4 grams (0.29 mole) sodium hydroxide, 26.5 grams (0.35 mole) sodium hydrosulfide (73.1% by weight active compound) and 73.0 grams water. The solution was heated at 95° C. for 20 minutes and then cooled to 60° C. Concentrated hydrochloric acid (12.0 grams) was added, while purging with nitrogen, over a one hour time period. After cooling to 30° C., the mixture was filtered and an aqueous solution of 20% by weight of zinc sulfate (113.0 grams; 0.14 mole of active compound) was added with stirring. The product was filtered to give 154.1 grams (wet cake). Color parameters were determined using a Hunter Color/Difference meter. A portion was dried and analyzed for zinc pyrithione content. A yield of 84.4% (assaying 96.2% pure) was obtained. The measured color parameters and calculated Whiteness were: L=92.9; a=−2.1; b=7.5; W=46.4.

EXAMPLE III

To an aqueous solution of 2-chloropyridine-N-oxide (149.5 grams of solution; 0.30 mole of active compound) and 37.8 grams (0.36 grams) sodium carbonate at 50° C. was added an aqueous solution of 73.1% by weight sodium hydrosulfide (25.3 grams; 0.33 mole) in 50.0 grams water. The solution was stirred at 90° C. for 0.5 hour and then cooled to 60° C. Concentrated hydrochloric acid (51.0 grams) was added, while purging with nitrogen, over a one hour time period. After cooling to 30° C., the mixture was filtered and an aqueous solution of 20% by weight zinc sulfate (120.0 grams of solution; 0.15 mole of active compound) was added with stirring. The product was filtered to give 153.0 grams (wet cake). Color parameters were determined using a Hunter Color/Difference meter. A portion was dried and analyzed for zinc pyrithione content. A yield of 88.9% (assaying 96.2% pure) was obtained. The measured color parameters and calculated Whiteness were: L=93.6; a=−1.7; b=6.8; W=51.4.

The comparison of the results of Example III and Comparison III shows that the Carbonate Procedure gives a better yield and a whiter product.

COMPARISON III

To the same aqueous solution of 2-chloropyridine-N-oxide as used in Example III (149.5 grams of solution; 0.30 mole of active compound) at 50° C., in a reaction vessel, was added an aqueous solution containing 11.4 grams (0.29 mole) sodium hydroxide, 26.2 grams (0.34 mole) sodium hydrosulfide (73.1% by weight active compound), and 84.4 grams water. The solution was stirred at 95° C. for 20 mins. and then cooled to 60° C. Concentrated hydrochloric acid (11.3 grams) was added, while purging with nitrogen, over a one hour time period. After cooling to 30° C., the mixture was filtered and an aqueous solution of 20% by weight of zinc sulfate (119.2 grams of solution; 0.15 mole of active compound) was added with stirring. The product was filtered to give 150.2 grams (wet cake). Color parameters were determined using a Hunter Color/Difference meter. A portion was dried and analyzed for zinc pyrithione content. A yield of 81.6% product (assaying 96.1% pure) was obtained. The measured color parameters and calculated Whiteness were: L=95.0; a=−3.2; b=8.6; W=43.3.

EXAMPLES IV–VIII AND COMPARISON IV

Mercaptization Caustic/Carbonate Method

Using the procedure described in Examples I to III, various mixtures of sodium hydroxide/sodium carbonate were employed in the mercaptization of the same batch of 2-chloropyridine-N-oxide (although a different batch than from the preceding Examples) and the resulting sodium pyrithione was converted to zinc pyrithione. The results are shown in Table I. These results show the benefit of carbonate in decreasing the b values and in increasing Whiteness values W (increasing white color of the product). An added benefit is the reduction of by-product 2-hydroxypryidine-N-oxide.

TABLE I

| Comparison and Example No. | Moles/Mole 2-Chloropyridine-N—Oxide | | | Assay (%)* 2-Hydroxypyridine-N—Oxide | Color Parameters and Whiteness | | | |
|---|---|---|---|---|---|---|---|---|
| | NaSH | NaOH | Na₂CO₃ | | L | a | b | W |
| C-IV | 1.20 | 1.00 | — | 1.03 | 91.3 | −5.5 | 9.0 | 36.9 |
| E-IV | 1.20 | 0.84 | 0.13 | 0.67 | 93.6 | −5.5 | 8.0 | 44.9 |
| E-V | 1.20 | 0.60 | 0.25 | 0.63 | 95.8 | −6.3 | 7.8 | 49.2 |
| E-VI | 1.20 | 0.40 | 0.37 | 0.44 | 95.7 | −6.2 | 8.0 | 47.5 |
| E-VII | 1.20 | 0.50 | 0.50 | 0.38 | 93.6 | −5.9 | 7.8 | 46.2 |
| E-VIII | 1.20 | — | 1.50 | 0.40 | 95.1 | −5.4 | 6.2 | 56.6 |

*in dry zinc pyrithione

What is claimed is:

1. A process for preparing zinc pyrithione comprising the steps:
 (a) adding sodium hydrosulfide and a base selected from the group consisting of sodium carbonate and sodium hydroxide to an aqueous solution of a 2-halopyridine-N-oxide selected from the group consisting of 2-bromopyridine-N-oxide and 2-chloropyridine-N-oxide, at a temperature below about 70° C.
   (i) wherein the mole ratio of the sum of moles of said sodium hydrosulfide and said base to said 2-halopyridine-N-oxide is at least about 2:1;

(ii) wherein the mole ratio of said sodium hydrosulfide to said 2-halopyridine-N-oxide is at least about 1:1;

(iii) wherein the mole ratio of said base to said 2-halopyridine-N-oxide is at least about 0.75:1; and (iv) wherein said base is comprised of at least about 10 mole % of sodium carbonate;

(b) heating the resultant mixture of step (a) to about 75° C. to about 105° C. for sufficient time to form sodium pyrithione; and (c) reacting said sodium pyrithione with a zinc salt to form zinc pyrithione.

2. The process of claim 1 wherein said 2-halopyridine-N-oxide is 2-chloropyridine-N-oxide.

3. The process of claim 1 wherein said base is 100 mole % of sodium carbonate.

4. The process of claim 3 wherein said sodium carbonate is added in solid form.

5. The process of claim 1 wherein the mole ratio of the sum of moles of said sodium hydrosulfide and base to said 2-halopyridine-N-oxide is from about 2:1 to about 3:1.

6. The process of claim 1, wherein the mole ratio of said sodium hydrosulfide to 2-halopyridine-N-oxide is from about 1:1 to about 1.25:1.

7. The process of claim 1, wherein the mole ratio of said base to said 2-halopyridine-N-oxide is from about 1:1 to about 1.2:1.

8. The process of claim 1, wherein the temperature at which said base and sodium hydrosulfide is added is from about 20° C. to about 65° C.

9. A process for preparing zinc pyrithione comprising the steps:

(a) adding sodium hydrosulfide and a base selected from the group consisting of sodium carbonate and sodium hydroxide to an aqueous solution of 2-chloropyridine-N-oxide at a temperature from about 20° C. to about 65° C.

(i) wherein the mole ratio of the sum of moles of said sodium hydrosulfide and said base to said 2-chloropyridine-N-oxide is from about 2:1 to about 3:1;

(ii) wherein the mole ratio of said sodium hydrosulfide to said 2-chloropyridine-N-oxide is from about 1:1 to about 1.25:1;

(iii) wherein the mole ratio of said base to said 2-chloropyridine-N-oxide is from about 1:1 to about 1.2:1; and (iv) wherein said base is comprised of at least about 10 mole % of sodium carbonate;

(b) heating the resultant mixture of step (a) to about 75° C. to about 105° C. for sufficient time to form sodium pyrithione; and (c) reacting said sodium pyrithione with a zinc salt to form zinc pyrithione.

10. The process of claim 9, wherein said base is 100 mole % of sodium carbonate.

11. The process of claim 10, wherein said sodium carbonate is added in solid form.

12. In a process for preparing sodium pyrithione which comprises reacting a 2-halopyridine-N-oxide with sodium hydrosulfide and a base to form sodium pyrithione, the improvement which comprises (a) adding said sodium hydrosulfide and a base selected from the group consisting of sodium carbonate and sodium hydroxide to an aqueous solution of a 2-halopyridine-N-oxide selected from the group consisting of 2-bromopyridine-N-oxide and 2-chloropyridine-N-oxide, at a temperature below about 70° C.

(i) wherein the mole ratio of the sum of moles of said sodium hydrosulfide and said base to said 2-halopyridine-N-oxide is at least about 2:1;

(ii) wherein the mole ratio of said sodium hydrosulfide to said 2-halopyridine-N-oxide is at least about 1:1;

(iii) wherein the mole ratio of said base to said 2-halopyridine-N-oxide is at least about 0.75:1; and (iv) wherein said base is comprised of at least about 10 mole % of sodium carbonate;

(b) heating the resultant mixture of step (a) to about 75° C. to about 105° C. for sufficient time to form said sodium pyrithione.

* * * * *